United States Patent [19]

Roberts et al.

[11] Patent Number: 4,921,706

[45] Date of Patent: May 1, 1990

[54] UNILAMELLAR LIPID VESICLES AND METHOD FOR THEIR FORMATION

[75] Inventors: Mary P. Roberts, Newton; Nancy E. Gabriel, Wellesley, both of Mass.

[73] Assignee: Massachusetts Institute of Technology, Cambridge, Mass.

[21] Appl. No.: 673,357

[22] Filed: Nov. 20, 1984

[51] Int. Cl.$^5$ .................. A61K 9/66; A61K 37/22; B01J 13/02

[52] U.S. Cl. .................. 424/450; 260/403; 264/4.1; 264/4.6; 424/1.1; 424/7.1; 428/402.2; 436/829

[58] Field of Search .................. 264/4.1, 4.6; 428/402.2; 424/38, 450; 436/829; 260/403

[56] References Cited

U.S. PATENT DOCUMENTS

| | | | |
|---|---|---|---|
| 4,217,344 | 8/1980 | Vanlerberghe et al. | 428/402.2 X |
| 4,224,179 | 9/1980 | Schneider | 264/4.6 |
| 4,263,286 | 4/1981 | Nakajima et al. | 260/403 X |
| 4,310,505 | 1/1982 | Baldeschwieler et al. | 424/1.1 |
| 4,310,506 | 1/1982 | Baldeschwieler et al. | 424/1.1 |
| 4,372,949 | 2/1983 | Kodama et al. | 424/38 X |
| 4,427,649 | 1/1984 | Dingle et al. | 424/38 |
| 4,515,736 | 5/1985 | Deamer | 264/4.6 X |

FOREIGN PATENT DOCUMENTS 0088046 9/1983 European Pat. Off. .............. 264/4.1

OTHER PUBLICATIONS

Gabriel, N. E. and M. F. Roberts, Spontaneous Formation of Stable Unilamellar Vesicles, *Biophysical Journal*, 45:41A (1984).

Gabriel, N. E. and M. F. Roberts, Spontaneous Formation of Stable Unilamellar Vesicles, *Biochemistry*, 23:4011–4015 (1984).

Hauser, H. and N. Gains, Spontaneous Vesiculation of Phospholipids: A Simple and Quick Method of Forming Unilamellar Vesicles, *Proceedings of the National Academy of Science USA*, 79:1683–1687 (Mar. 1982).

Hauser, H. et al., Vesiculation of Unsonicated Phospholipid Dispersions Containing Phosphatidic Acid by pH Adjustment: Physiocochemical Properties of the Resulting Unilamellar Vesicles, *Biochemistry*, 22: 4775–4781 (1983).

Gains, N. and H. Hauser, Characterization of Small Unimellar Vesicles Produced in Unsonicated Phosphatidic Acid and Phosphatidylcholine-Phosphatidic Acid Dispersion by pH Adjustment, *Biochimica et Biophysica Acta*, 731:31–39 (1983).

Hope, M. H. et al., $Ca^{2+}$ and pH Induced Fusion of Small Unilamellar Vesicles Consisting of Phosphatidylethanolamine and Negatively Charged Phospholipids: A Freeze Fracture Study, *Biochemical and Biophysical Research Communications*, 1101:(1):15–22 (Jan. 14, 1983).

Szoka, Jr., F. and D. Papahadjopoulos, Comparative Properties and Methods of Preparation of Lipid Vesicles (Liposomes), *Ann. Rev. Biophys., Bioeng,* 9:467–508 (1980).

Shek, P. N. et al., Comparison Between Multilamellar and Unilamellar Liposomes in Enhancing Antibody Formation, *Immunology*, 1983 49:37–44 (1983).

Hub, H. H. et al., Preparation of Large Unilamellar Vesicles, *FEBS Letters*, 140:2 (Apr. 1982).

Roseman, M. A. et al., Properties of Sonicated Vesicles of Three Synthetic Phospholipids, *Chemistry and Physics of Lipids*, 211:205–222 (1978).

*Primary Examiner*—Richard D. Lovering
*Attorney, Agent, or Firm*—Hamilton, Brook, Smith & Reynolds

[57] ABSTRACT

This invention relates to unilamellar lipid vesicles comprised of short-chain phospholipids and long-chain phospholipids and a method for making the vesicles. The short-chain phospholipids are comprised of fatty acids with fewer than 9 carbons atoms and the long-chain phospholipids are comprised of fatty acids with at least 12 carbon atoms.

37 Claims, 1 Drawing Sheet

U.S. Patent May 1, 1990 4,921,706
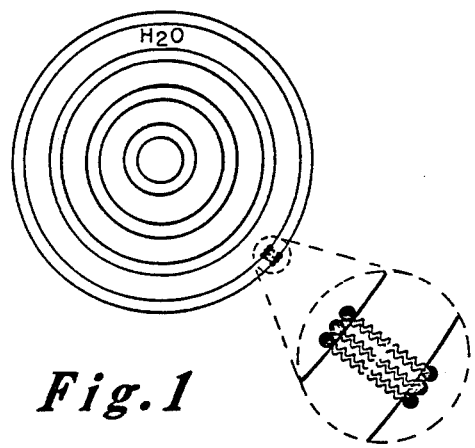
*Fig.1*
*Fig.1A*
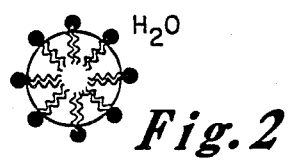
*Fig.2*
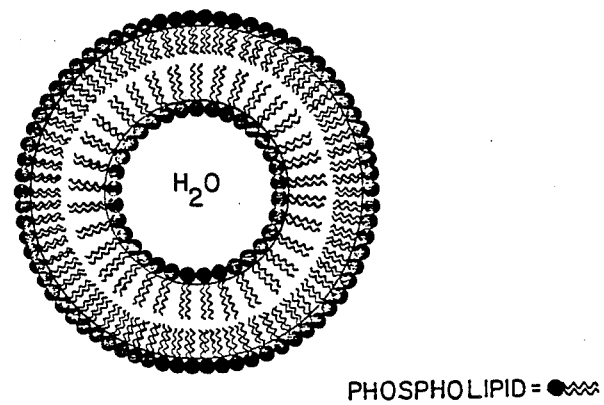
PHOSPHOLIPID =
*Fig.3*

UNILAMELLAR LIPID VESICLES AND METHOD FOR THEIR FORMATION

GOVERNMENT SUPPORT

The invention described herein was supported by a grant from the National Institutes of Health.

TECHNICAL FIELD

This invention is in the fields of chemistry and biochemistry and in particular relates to the formation of unilamellar lipid vesicles.

BACKGROUND ART

Lipids make up a group of biological substances which have in common their insolubility in water and high solubility in organic solvents (e.g., chloroform). They have several important biological roles, such as serving as components of membranes, providing fuel and functioning as highly concentrated energy stores.

Phospholipids make up one of the four major groups of membrane lipids; glycolipids, cholesterol and glyceride derivatives (e.g., triglycerides, diglycerides, monoglycerides and component fatty acids) are the others. Phospholipids are derived from the three-carbon alcohol, glycerol, or from a more complex alcohol, sphingosine. Those derived from glycerol are called phosphoglycerides and occur almost exclusively in cell membranes. A phosphoglyceride is comprised of a glycerol backbone, two fatty acid chains and a phosphorylated alcohol. One of the primary hydroxyl groups of glycerol is esterified to phosphoric acid; a polar head group, an alcohol represented by X—OH, is esterified to the phosphoric acid through its hydroxyl group. Commonly occurring alcohol components of phosphoglycerides are choline, ethanolamine, serine, glycerol and inositol. The resulting phospholipids are called, respectively, phosphatidylcholine (PC), phosphatidylethanolamine (PE), phosphatidylserine (PS), diphosphatidylglycerol (PG) and phosphatidylinositol (PI). The two remaining hydroxyl groups of the glycerol backbone are esterified to fatty acids, which may be saturated or unsaturated. These hydrocarbon tails are nonpolar in nature.

Phospholipids containing sphingosine (or a related base) as their backbone are called sphingolipids and are components of plant and animal cell membranes. These phospholipids have three characteristic components: a fatty acid; sphingosine or a related derivative; and a polar head group. In higher animals, sphingomyelins are the most commonly occurring sphingolipids. They contain phosphorylcholine or phosphorylethanolamine as the polar head groups and exhibit physical properties similar to those of PC and PE.

Because they have a polar head group and nonpolar hydrocarbon tails, phospholipids are amphiphilic (also called amphipathic) or polar lipids. In water or other aqueous medium, the polar head groups exhibit their affinity for water and the hydrocarbon chains avoid water. This can be achieved in at least two ways: by forming micelles or by forming a lipid bilayer (or biomolecular sheet). Short-chain phospholipids (those with fatty acids of fewer than 9 carbon atoms) form micelles when dispersed in aqueous solutions. R. J. M. Tausk et al., *Biophysics and Chemistry*, 1:175-183(1974); R. J. M. Tausk et al., *Biophysics and Chemistry*, 2:53-63 (1974). In a micelle, the polar head groups are on the surface and the hydrocarbon chains aligned inside the structure. On average, the terminal methyl group of the fatty acyl chains is at the center of the hydrophobic sphere, ellipsoid or cylindrical structure.

The lipid bilayer configuration is formed rapidly when long-chain phospholipids are placed in water. Because of their amphiphilic nature, the lipid molecules arrange themselves spontaneously into the bilayer configuration. In the bilayer, the polar head groups are at the two surfaces of the bilayer and the hydrophobic hydrocarbon chains are sequestered in the bilayer interior.

Lipid bilayers are held together by several noncovalent interactions and exposure of hydrocarbon chains to the aqueous medium is minimized. Lipid bilayers tend to close on themselves so that there will be no ends, and thus no hydrocarbon chains exposed to the aqueous medium. This results in the formation of a lipid-enclosed aqueous compartment. In addition, the bilayers tend to be self-sealing; a hole in the bilayer is energetically unfavorable.

The term liposome or lipid vesicle refers to the lipid bilayers and the encapsulated aqueous compartment. When long-chain phospholipids (e.g., PC, PS, PE, phosphatidic acid) are dispersed in an aqueous solution, they spontaneously form large multilamellar structures. These structures consist of many concentric layers of lipid, which have aqueous phases interspersed between the bilayers. B. E. Ryman and D. A. Tyrrell, "Liposomes—Bags of Potential," In: *Essays in Biochemistry*, P. N. Campbell and R. D. Marshall (ed.), Academic Press, London, 49-98. (1980). These multilamellar vesicles (MLVs) may also be formed by the addition of an aqueous phase to a dry lipid film (e.g., egg phosphatidylcholine), followed by gentle agitation.

A wide variety of lipids has been used in liposome preparations (Table I). Usually PC or sphingomyelin is the major lipid and small amounts of other species (e.g., charged amphiphiles such as stearylamine, dicetylphosphate) are added.

TABLE I
Lipids Used in Liposome Preparation

| Lipid | Comments |
| --- | --- |
| Egg Phosphatidylcholine | Most commonly used major component |
| Dipalmitoyl-PC | Synthetic fully saturated phosphatidylcholine |
| Distearoyl-PC | Less permeable to aqueous phase than egg PC |
| Sphingomyelin | Often preferred to egg PC in immunological studies; improves liposome stability in vivo |
| Cholesterol | Reduces permeability of egg PC vesicles; maximum incorporation of 50 mol % with phospholipids |
| Stearylamine | Imparts net positive charge; not naturally occurring; may be toxic to cells |
| Phosphatidic acid | Imparts net negative charge |
| Phosphatidylserine | Imparts net negative charge |
| Cardiolipin | Antigenic lipid used in immunological applications |
| Phosphatidylethanolamine | Does not form enclosed |

TABLE I-continued

| Lipid | Comments |
|---|---|
| | vesicle on its own; useful for coupling materials to the external surface of liposomes; substituted derivatives are used in immunological studies |
| Lysophosphatidylcholine | Increases liposome permeability; may enhance liposome fusion with cells |

Unilamellar vesicles—which are aqueous compartments surrounded by only one shell of lipid bilayer—may be formed from the multibilayers (MLVs). Several methods have been developed for forming unilamellar vesicles from MLVs. F. Szoka and D. Papahadjopoulos, Comparative Properties and Methods of Preparation of Lipid Vesicles (Liposomes), *Annual Review of Biophysics and Bioengineering*, 9:467–508. (1980). Each, however, either requires special equipment or involves nonphospholipid material (e.g., organic solvents, detergents) and is a multistep process. One of these methods involves sonication—agitation by high-frequency sound waves—of an aqueous suspension of a suitable lipid. D. Papahadjopoulos and H. K. Kimelberg, *Progress in Surface Science*, W. G. Davison (ed.), Pergamon Press, 4:139–221, (1973). Alternative methods for producing unilamellar vesicles include reverse phase evaporation from organic solvent, F. Szoka, Jr. and D. Papahadjopoulos, *Proceedings of the National Academy of Sciences, U.S.A.* 75:4194–4198, (1978); detergent dialysis or dilution, J. Brunner et al., *Biochimica et Biophysica Acta*, 455:322–331, (1976); and pressure/mechanical filtration. R. Hamilton et al., *Journal of Lipid Research*, 21:981–992, (1980); M. C. Farmer and B. P. Gaber, *Biophysics*, 45:41a, (1984). These methods were developed for producing unilamellar vesicles from MLVs containing PCs and have not been extensively used with other phospholipids. Often, the vesicles produced by altering the MLVs using these methods are not stable; tend to aggregate or fuse; and are likely to release their contents.

Gains and Hauser report a method of forming small unilamellar vesicles from a solution of dilauroyl phosphatidic acid or mixtures of dilauroyl phosphatidic acid and PC in chloroform/methanol. N. Gains and H. Hauser, Characterization of Small Unilamellar Vesicles Produced in Unsonicated Phosphaticid Acid and Phosphatidylcholine-Phosphatidic Acid Dispersions by pH Adjustment, *Biochimica et Biophysica Acta*, 731:31–39 (1983). The method involves formation of a film from such a solution, dispersing the film in water or an aqueous solution containing sodium chloride and sulfate ions; raising the pH of the solution by titration with sodium hydroxide; and subsequent lowering of the pH. It is claimed that as the pH of the solutions is raised, vesicles are formed because the phosphate group of the phosphatidic acid molecules becomes ionized. This method is not generally applicable as a means of producing unilamellar vesicles, however. It requires the presence of the anionic phospholipid phosphatidic acid and cannot be used to produce PC or PE unilamellar vesicles. The pH shifts necessary to form the vesicles according to this method limit its use because many proteins and other substances to be encapsulated in the vesicles will be unstable to or adversely affected by such shifts.

Substances may be entrapped or incorporated into liposomes in a number of ways and therefore liposomes have great potential in a wide variety of fields. For example, in medicine there has long been a need for biodegradable vehicles or carriers for therapeutic materials because such materials may be toxic unless they are incorporated into a carrier or delivery vehicle; are degraded by the body before they reach their target; or are diffused throughout the body, instead of being delivered to a desired target site. MLVs may be useful for this delivery or protection purpose but are usually too large for effective dispersal. Alternatively, MLVs may be processed by one or more of the existing methods to produce unilamellar vesicles, which are more suitable for these purposes.

Current methods of producing unilamellar vesicles, however, are far less than satisfactory because they require specialized equipment, involve nonphospholipid materials which might contaminate or alter the resulting lipid vesicle - entrapped substance combination and/or are time consuming because they require multiple steps. The unilamellar vesicles produced by these methods are also often or typically less than satisfactory because of their instability (which often depends on vesicle curvature and size), tendency to aggregate and release of the entrapped material. Of the methods available for making small unilamellar vesicles, only two—sonication and extrusion through a French press—give good encapsulation efficiencies. However, both methods require specialized equipment and several steps. In methods which involve detergent removal, much of the drug to be encapsulated is likely to be lost before the vesicles are formed.

DISCLOSURE OF THE INVENTION

The subject of this invention is unilamellar lipid vesicles which are spontaneously formed upon the mixing of aqueous suspensions of short-chain phospholipids (i.e., having fatty acid chain lengths of fewer than 9 carbons) with aqueous suspensions of long-chain phospholipids (i.e., having fatty acid chain lengths of at least 12 carbon atoms). The vesicles are easily formed, stable, non-leaky (i.e., do not release their contents) and cover a wide size range.

The subject of this invention is also the method of forming these stable unilamellar lipid vesicles. The method comprises the mixing of aqueous suspensions of long-chain phospholipids with aqueous suspensions of short-chain phospholipids or hydration of dried lipid films. It takes advantage of the difference in fatty acid chain length of the phospholipids used and packing of the hydrophobic chains to minimize contact with water. Short-chain phospholipids are inserted into the multibilayers formed by the long-chain phospholipids and unilamellar vesicles are formed. The method is very simple, does not require special equipment or nonphospholipid materials, and produces stable, non-leaky unilamellar vesicles.

BRIEF DESCRIPTION OF THE DRAWINGS

FIG. 1 is a schematic representation of a multilamellar vesicle (MLV). FIG. 1 represents such a vesicle and FIG. 1A is an enlarged section of the vesicle.

FIG. 2 is a schematic representation of a micelle.

FIG. 3 is a schematic representation of a unilamellar vesicle.

BEST MODE OF CARRYING OUT THE INVENTION

The vesicles produced by the method of this invention may be used for the delivery of drugs and other substances to specific sites in the body. The unilamellar vesicles produced by presently available methods are not satisfactory because they are unstable, tend to aggregate and release the entrapped material. In contrast, the vesicles of the present invention are easily formed, stable and non-leaky. As a result, they have significant advantages as a means of entrapping drugs and related substances and delivering them to specific sites within the body, for example for therapeutic or diagnostic purposes.

In one embodiment of this invention, stable unilamellar vesicles are formed spontaneously when films of short-chain phospholipids and long-chain phospholipids formed by evaporation of organic solvent from a solution of such phospholipids, are dispersed in an aqueous medium. The short-chain phospholipids comprise fatty acids having fewer than 9 carbons. For example, they may be comprised of fatty acids having 6–8 carbon atoms, such as dihexanoyl phosphatidylcholine, diheptanoyl phosphatidylcholine, or dioctanoyl phosphatidylcholine. The long-chain phospholipids, which are the basic bilayer matrix, can comprise any saturated or unsaturated phospholipids comprised of fatty acids which have at least 12 carbon atoms.

In this embodiment, the short-chain and the long-chain phospholipids are co-solubilized in an organic solvent, such as chloroform ($CHCl_3$). After brief mixing, nitrogen gas is blown over the surface of the solution to agitate it and to evaporate most of the organic solvent. As a result, a film containing the short-chain phospholipids and the long-chain phospholipids is deposited on the walls of the container. The container is then placed on a lyophilizer and any remaining traces of organic solvent removed by evacuation at low pressure. In one embodiment of this invention, the low pressure is approximately 100 microns or less and evacuation is carried out for at least 8 hours.

Stable unilamellar vesicles are produced when the film formed from the short- and the long-chain phospholipids is dispersed in an aqueous solvent. The aqueous solvent may contain sodium chloride. In one embodiment, the aqueous solvent contains about 0.15M sodium chloride (physiological salt concentration). In one embodiment, in which the short-chain phospholipid is dioctanoyl-PC, the film may be dispersed in an aqueous solvent containing about 0.2M potassium thiocyanate (KSCN) or a similar "salting in" compound (e.g., lithium iodide). The aqueous solvent containing KSCN may be used alone or in an aqueous solvent which also contains sodium chloride. Optionally, the hydrated samples may be bath sonicated for about one minute for the purpose of mixing, prior to equilibration. The bath sonication procedure is not sufficient to form unilamellar vesicles from MLVs. The resulting solution is then equilibrated. Equilibration is carried out by letting the solution stand undisturbed. In one embodiment, equilibration is carried out at room temperature (i.e., about 20°–25° C.) for at least 6 hours.

In another embodiment of this invention, unilamellar vesicles are formed when aqueous solutions of short-chain phospholipids (e.g., having fatty acid chain lengths of fewer than 9 carbon atoms) are incubated with aqueous solutions of multibilayers comprised of long-chain phospholipids (e.g., having fatty acids whose chains are at least 12 carbon atoms in length). In this embodiment, the short-chain phospholipid and the long-chain phospholipid are solubilized separately (i.e., in separate containers) in an organic solvent, such as $CHCl_3$.

Each of the phospholipids solubilized in organic media is then treated as in the previous embodiment. After brief mixing, nitrogen gas is blown over the top of each solution to agitate it and evaporate most of the organic solvent. The phospholipids are deposited on the walls of the respective containers, which are placed on a lyophilizer. Remaining traces of organic solvent are removed by evacuation at low pressure. In one embodiment of this invention, the low pressure is approximately 100 microns or less and evacuation is carried out for at least 8 hours.

Each phospholipid-containing film is then dispersed in an aqueous solvent, which may contain sodium chloride. In one embodiment, the aqueous solvent contains about 0.15M sodium chloride (physiological salt concentration). In one embodiment, in which the short-chain phospholipid is dioctanoyl phosphatidylcholine, the film is dispersed in an aqueous solvent containing about 0.2M KSCN, which may be used alone for hydration or in an aqueous solvent which also contains sodium chloride. Optionally, the hydrated samples may be bath sonicated for about one minute for the purpose of mixing.

Unilamellar vesicles spontaneously form when a small amount (typically about 20 mol % total lipid) of the solution containing short-chain phospholipids is added to the solution containing long-chain phospholipid (the multibilayer) and the resulting solution mixed (e.g., by being shaken by hand or vortexed) and allowed to equilibrate. In one embodiment, equilibration is carried out at room temperature (i.e., about 20°–25° C.) for at least 6 hours.

The solutions of short-chain and long-chain phospholipids used to form the unilamellar lipid vesicles of this invention may also contain relatively small amounts (i.e., less than about 10 mol %) of components such as cholesterol, stearylamine, phosphatidic acid, cardiolipin and lysophosphatidylcholine.

Data from Nuclear Magnetic Resonance (NMR) spectroscopy and fluorescence spectroscopy were obtained for the vesicles produced by the method of this invention. Data from the NMR spectroscopy provided evidence that the resulting vesicles are comprised of both the short-chain and the long-chain phospholipids (e.g., that the short-chain phospholipids became incorporated with the long-chain phospholipids in the bilayer) and are unilamellar in structure. The $^1$H-NMR data are consistent with unilamellar vesicles equal to or greater than 300 Angstroms in diameter. This is also confirmed by quasielectric light-scattering measurements and at least one electron micrograph. Data from the fluorescence spectroscopy of vesicles loaded with self-quenching concentrations of dyes provided proof of the stability or integrity of the vesicles.

$^1$H-NMR SPECTRAL FEATURES OF LECITHIN MIXTURES

500 MHz $^1$H-NMR spectra were obtained on a home-built spectrometer at the Francis Bitter National Magnet Laboratory, M.I.T. Twenty transients with a 90° flip angle (15 microsec) and 5 sec repetition time were collected and transformed with a 1.0 Hz exponential weighting function. Spin-lattice relaxation times were measured by inversion-recovery R. L. Vold et al., *Journal of Chemical Physics*, 48:3839, (1968). Lanthanide shift experiments were done by adding amounts of 5 mM or 20 mM $Pr^{3+}$ (as praesodymium chloride, $PrCl_3.6H_2O$) stock solution to 0.3 ml samples at pH 6.5–7.

When dipalmitoyl-PC and diheptanoyl-PC are co-solubilized in organic solvent in a 4:1 ratio, solvent removed, and the film rehydrated with an aqueous solution to yield a 20 mM/5 mM mixture, an opalescent solution is produced. At lower temperatures it is often slightly cloudy, but it can be clarified with a little heat. By comparison, 20 mM dipalmitoyl-PC hydrated with an aqueous solution is milky white and a solution of a short-chain phosphatidylcholine is optically clear. Similar procedures have been carried out for vesicles made from the other PCs which are the subject of this invention and the data described here are presented only as one example.

The slightly cloudy to opalescent appearance of the solution of the long-chain/short-chain mixture is different from the appearance of either the solution containing only a short-chain PC (e.g., diheptanoyl-PC) or the solution containing only a long-chain PC (e.g., dipalmitoyl-PC). The appearance of the long-chain/short-chain mixtures is intermediate that of the other two solutions.

The long-chain/short-chain mixture gives rise to high resolution NMR spectra. At all temperatures, linewidths are narrower than for multibilayer dispersions, but broader than for short-chain PC micelles R. D. Hershberg et al., *Biochimica et Biophysica Acta*, 424:73–81, (1976). Thus, the mixture is different in this respect from the long-chain PC solution and the short-chain PC solution. Here, too, the characteristics of the mixture are intermediate between those of the two solutions. In general, all resonances broaden as the temperature is increased toward the dipalmitoyl-PC phase transition temperature of 41° C., then narrow. As an example, the bulk methylene resonance (about 1.35 ppm) of diheptanoyl-PC/dipalmitoyl-PC vesicles broadens from 57 Hz at room temperature to 106 Hz at 40° C., and then narrows above that temperature (95 Hz at 45° C.). Clear splitting is observed for the $N(CH_3)_3$ group below 41° C.; this is most prominent at room temperature. With an increase in temperature the two resonances shift downfield differentially such that they coalesce around 40° C. (near the dipalmitoyl-PC phase transition temperature). Above that temperature the linewidth of the $N(CH_3)_3$ peak narrows, and occasionally two discrete resonances can again be discerned.

There are several possible explanations for the observed splitting in the $N(CH_3)_3$ region. In order to determine which of these alternatives is correct, similar PC mixtures using $N(CD_3)_3$-dipalmitoyl-PC and diheptanoyl-PC were prepared and analyzed. Only one narrow resonance is visible in the choline methyl region; this can only arise from the short-chain lecithin. Therefore, the two resonances observed when both components are the proteo species are due to the chemically and possibly environmentally distinct diheptanoyl-PC and dipalmitoyl-PC. The narrower resonance belongs to the short-chain species. As the temperature increases the single diheptanoyl-PC resonance shifts downfield (about 20 Hz/5°), but not as rapidly as the component from dipalmitoyl-PC which eventually obscures and then overtakes it.

Similar spectra are produced if micellar diheptanoyl-PC (5 mM) is added to multibilayer dispersions of dipalmitoyl-PC (20 mM). Within four minutes of mixing the two aqueous solutions, high resolution spectral features are apparent. Initially resonances are broad, but narrow on the time scale of hours. After seven hours at room temperature the mixture has reached equilibrium, as evidenced by the fact that no further spectral changes occur.

$^1H$ spin-lattice relaxation times, $T_1$, obtained for pure diheptanoyl-PC micelles and a mixed PC mixture provide evidence that the short-chain PC is not present as a micelle (or monomer). It also provides evidence that there is mixing of short-chain PC with the long-chain PC bilayer (i.e., that the vesicles are made from both). For bulk methylene and terminal methyl groups (as well as $N(CH_3)_3$) in the mixed particles, two components are observed in the $^1H$ NMR spectrum at room temperature. While $N(CH_3)_3$ $T_1$ values are not very structure dependent, $T_1$ values for the chain protons differ dramatically. The short-chain PC in the mixed particles has shorter $T_1$ values than in pure PC micelles ($T_1$ values for monomers would be even longer). This is best illustrated with the diheptanoyl-PC terminal methyl group. Its $T_1$ is 1.26 sec in micelles, and 0.87 sec when mixed with dipalmitoyl-PC at 25° C. In the mixed particle the diheptanoyl-PC methyl $T_1$ is also significantly less than the corresponding dipalmitoyl-PC methyl (1.07 sec). This may reflect some type of motional restraints on heptanoyl chains by neighboring palmitate chains.

DETECTION OF BILAYER VESICLES

The types of particles present in solution could be multibilayers, unilamellar vesicles, or mixed micelles. It is unlikely that the dominant type is multibilayers, in light of the clarity of the solution. Lanthanide shift reagents can be used to distinguish between vesicle and micellar or monomer species. $Pr^{3+}$ added to a population of vesicles complexes with the phospholipid headgroup and shifts resonances from molecules in the outer layer of the bilayer downfield without affecting resonances from phospholipid molecules in the bilayer interior. If all phospholipid head-groups are exposed to the exterior $Pr^{3+}$ solution (which would be the case for micelles or monomers), then all resonances will be shifted; a different shift increment might be evident for short-chain versus long-chain species.

$^1H$-NMR (500 MHz) lanthanide shift experiments to detect vesicles were undertaken at temperatures above and below the $T_c$ of the long-chain lecithin. Results showed that the resonance from diheptanoyl-PC does not vary when small amounts of $Pr^{3+}$ are added. In contrast, the broader dipalmitoyl-PC resonance splits into two peaks. The most downfield-shifted of these is due to the exterior monolayer of dipalmitoyl-PC. The upfield, broader peak is due to the interior layer dipalmitoyl-PC. The intensities of the two dipalmitoyl-PC peaks are approximately equal, indicating that the vesicles are unilamellar. (If they were multilamellar, only the outermost layer PC molecules would be exposed to $Pr^{3+}$; for two layers, the outer/inner ratio would be 1:3, etc.) With further addition of $Pr^{3+}$ to concentrations which cause a shift in pure micelles of diheptanoyl-PC, the $N(CH_3)_3$ resonance of the short-chain component in the vesicles also shifts downfield, but not as much as for micellar samples. At that level of $Pr^{3+}$, the dipalmitoyl- PC peaks are broadened dramatically. Two discrete short-chain peaks are not observed under these conditions. This suggests that the short-chain species is either all on the outer surface and interacts more weakly with $Pr^{3+}$ than dipalmitoyl-PC, or is rapidly exchanging across the bilayer. Similar results are seen for other diheptanoyl-PC/long-chain lecithin (dimyristoyl-PC, distearoyl-PC, egg lecithin) mixtures both above and below the phase transition temperature of the long-chain species. Preliminary quasielastic light scattering experiments detect particle distributions which are bimodal or more complex for temperatures below the $T_c$ and about 610 Angstroms (variance=0.2) for diheptanoyl-PC/dipalmitoyl-PC vesicles at 45° C. This represents a very homogenous distribution of vesicle sizes.

VESICLE STABILITY

Stability (integrity) studies were conducted by encapsulating the fluorescent dye 6-carboxyfluorescein inside the vesicles. At high concentrations, fluorophores undergo self-quenching collisions which decrease the fluorescence intensity emitted from the solution Dilution of the dye results in an increase in fluorescence intensity. If dye leakage occurs from vesicles it will result in substantial dilution (due to the small internal volume of the vesicles compared with the total sample volume) of the dye with consequent increase in fluorescence. A Perkin-Elmer LS-3 fluorescence spectrometer was used to measure fluorescence of 6-carboxyfluorescein at room temperature: $\lambda_{max}=490$ nm, $\lambda_{em}=520$ nm. Mixed lipid films were hydrated in the presence of 100 mM 6-carboxyfluorescein. Most of the free dye was separated from entrapped dye by passage through a (0.9×21.5 cm) Sephadex G-25 fine column. The solution collected in the void volume contained vesicles with entrapped dye. The ratio of fluorescence in each vesicle sample compared to the Triton X-100 mixed micelle standard was monitored for diheptanoyl-PC/dipalmitoyl-PC vesicles made and stored at 4° C., 25° C. and 45° C. A three-fold increase in fluorescence above background was observed for the samples to which Triton X-100 was added. At 4° and 25° C. this may not be enough Triton to micellize dipalmitoyl-PC completely, but it should cause at least partial micellization. A. A. Ribeiro et al., *Biochimica et Biophysica Acta*, 332:26–29. (1974). The vesicle sample fluorescence remained unchanged for at least 5 days; an increase in the fluorescence ratio is detected as the vesicles aggregate. This is most pronounced for the sample formed and stored at 25° C. On the same time scale empty vesicles do not aggregate so that the clumping must reflect electrostatic interactions of dye loaded in the vesicles.

NMR experiments also suggest excellent vesicle stability. Samples stored with $Pr^{3+}$ for up to 2 weeks show no large change in the relative amount of outer/inner resonances. Initial preparations of vesicles are also stable to dilution at least 5-fold as judged by no change in the appearance of the $^1$H-NMR spectra under these conditions. (Any release of monomer short-chain PC would give rise to very narrow peaks as has been seen for bile salt-PC vesicle formation (Stark, R. E., Goslin, G., Roberts, M. F., and Carey, M., Biochemistry, in press).

The following examples are presented to illustrate the invention and for that purpose only. They are not intended to be limiting in any way.

EXAMPLE 1

Co-solubilization Method

Dipalmitoyl-PC (DPPC) in a chloroform stock solution and diheptanoyl-PC (DiC$_7$PC) in a separate chloroform stock solution are added to a vial such that the final DPPC concentration is 20 mM and the final DiC$_7$PC concentration is 5 mM. The vial walls are washed with about 1 ml of chloroform. The organic solvent is evaporated under a gentle stream of nitrogen such that the surface of the solution is agitated slightly. Traces of the organic solvent are removed by evacuating the sample for about 12 hours at a pressure of about 100 microns. An aqueous 0.15M NaCl solution is added to the vial such that the total lipid concentration is 25 mM. This mixture is bath sonicated for about 60 seconds. It is then allowed to stand at room temperature (i.e., about 20°–25° C.) for about 8 hours.

EXAMPLE 2

Aqueous Mixing Method

An aqueous solution of DPPC is prepared by adding DPPC stock solution in chloroform to a vial such that the final DPPC concentration is 20 mM. The organic solvent is evaporated away under a gentle stream of nitrogen such that the surface of the solution is agitated slightly. Traces of the organic solvent are removed by evacuating the sample for 12 hours at a pressure of 100 microns. An 0.15M aqueous NaCl solution is added to the vial. An aqueous solution may also be made by adding an aqueous 0.15M aqueous NaCl solution to solid DPPC. The mixture is bath sonicated for about 60 seconds and allowed to stand at room temperature (i.e., about 20°–25° C.) for about an hour.

An aqueous solution of DiC$_7$PC is prepared by adding DiC$_7$PC stock solution in chloroform (as supplied by, for example, Avanti) to a second vial such that the final DiC$_7$PC concentration is 50 mM. The DiC$_7$PC solution is then processed in the same way as the DPPC solution.

The 50 mM DiC$_7$PC aqueous solution is added to the 20 mM DPPC aqueous solution such that the final concentration of DiC$_7$PC is 5 mM. The solution is mixed by shaking. The mixture is allowed to stand at room temperature (i.e., about 20°–25° C.) for about 6–8 hours.

INDUSTRIAL APPLICABILITY

This invention has industrial applicability in the delivery of drugs for therapeutic or treatment purposes, for the delivery of drugs or reagents for diagnostic purposes (for example, for NMR imaging or radio label imaging) and for enzyme assays.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of forming unilamellar lipid vesicles, comprising the steps of:
   (a) forming a solution of short-chain phospholipids having fatty acids with 6 to 8 carbon atoms and long chain phospholipids having fatty acids with at least 12 carbon atoms in an organic solvent;

(b) removing organic solvent from the solution to form a residue;
(c) dispersing the residue in an aqueous medium; and
(d) equilibrating the resulting dispersion until unilamellar lipid vesicles have formed.

2. The vesicle produced by the method of claim 1.

3. The method of claim 1 additionally incorporating into the solution of short-chain phospholipids and long-chain phospholipids at least one additional component selected from the group consisting of: cholesterol, stearylamine, phosphatidic acid, cardiolipin and lysophosphatidylcholine.

4. The vesicle produced by the method of claim 3.

5. A method of forming unilamellar lipid vesicles, comprising the steps of:
(a) forming a film of short chain phospholipids having fatty acids with 6 to 8 carbon atoms and of long-chain phospholipids having fatty acids with at least 12 carbon atoms;
(b) dispersing the film in an aqueous medium; and
(c) equilibrating the resulting dispersion under conditions suitable for unilamellar lipid vesicles to form.

6. The vesicle produced by the method of claim 5.

7. A method of forming unilamellar lipid vesicles, comprising the steps of:
(a) forming a film of short-chain phospholipids having fatty acids with 6 to 8 carbon atoms; long-chain phospholipids having fatty acids with at least 12 carbon atoms and at least one additional component selected from the group consisting of: cholesterol, stearylamine, phosphatidic acid; cardiolipin and lysophosphatidylcholine;
(b) dispersing the film in an aqueous medium; and
(c) equilibrating the resulting dispersion under conditions suitable for unilamellar lipid vesicles to form.

8. The vesicle produced by the method of claim 7.

9. A method of forming unilamellar lipid vesicles, comprising the steps of:
(a) dissolving short-chain phospholipids having fatty acids with fewer than 9 carbon atoms and long-chain phospholipids having fatty acids with at least 12 carbon atoms in an organic solvent to form a solution thereof;
(b) evaporating the organic solvent under nitrogen to form a film of short-chain phospholipids and long-chain phospholipids;
(c) dispersing the film in an aqueous medium; and
(d) equilibrating the resulting dispersion until unilamellar lipid vesicles have formed.

10. The method of claim 9 in which the short-chain phospholipids have fatty acids with 6 to 8 carbon atoms.

11. The vesicle produced by the method of claim 10.

12. The method of claim 10, additionally incorporating into the solution of short-chain phospholipids and long-chain phospholipids in an organic solvent at least one additional component selected from the group consisting of: cholesterol, stearylamine, phosphatidic acid, cardiolipin and lysophosphatidylcholine.

13. The vesicle produced by the method of claim 12.

14. A method of forming unilamellar lipid vesicles, comprising the steps of:
(a) forming a solution of short-chain phospholipids having fatty acids with fewer than 9 carbon atoms in organic solvent;
(b) removing organic solvent to produce a first residue;
(c) dispersing the first residue in an aqueous medium;
(d) forming a solution of long-chain phospholipids having fatty acids with at least 12 carbon atoms in an organic solvent;
(e) removing organic solvent to produce a second residue;
(f) dispersing the second residue in an aqueous medium;
(g) combining the dispersion of the first residue and the dispersion of the second residue; and
(h) equilibrating the resulting dispersion until unilamellar lipid vesicles have formed.

15. The method of claim 14 in which the short-chain phospholipids are comprised of fatty acids having 6 to 8 carbon atoms.

16. The vesicle produced by the method of claim 14.

17. The method of claim 15, additionally incorporating into the solution of long-chain phospholipids in an organic solvent at least one additional component selected from the group consisting of: cholesterol, stearylamine, phosphatidic acid, cardiolipin and lysophosphatidylcholine.

18. The vesicle produced by the method of claim 17.

19. A method of forming unilamellar lipid vesicles, comprising the steps of:
(a) forming a film of short-chain phospholipids having fatty acids with fewer than 9 carbon atoms;
(b) dispersing the film of short-chain phospholipids in an aqueous medium;
(c) forming a film of long-chain phospholipids having fatty acids with at least 12 carbon atoms;
(d) dispersing the film of long-chain phospholipids in an aqueous medium;
(e) combining the dispersion of short-chain phospholipids and the dispersion of long-chain phospholipids; and
(f) equilibrating the resulting dispersion under conditions suitable for unilamellar lipid vesicles to form.

20. The method of claim 19 in which the short-chain phospholipids are comprised of fatty acids having 6 to 8 carbon atoms.

21. The vesicle produced by the method of claim 19.

22. A method of forming unilamellar lipid vesicles, comprising the steps of:
(a) forming a film of short-chain phospholipids having fatty acids with fewer than 9 carbon atoms;
(b) dispersing the film of short-chain phospholipids in an aqueous medium to form a first dispersion;
(c) forming a film of long-chain phospholipids having fatty acids with at least 12 carbon atoms and at least one additional component selected from the group consisting of: cholesterol, stearylamine, phosphatidic acid, cardiolipin and lysophosphatidylcholine;
(d) dispersing the film of long-chain phospholipids and at least one additional component in an aqueous medium to form a second dispersion;
(e) combining the first dispersion and the second dispersion; and
(f) equilibrating the resulting dispersion under conditions suitable for unilamellar lipid vesicles to form.

23. The method of claim 22 in which the short-chain phospholipids are comprised of fatty acids having 6 to 8 carbon atoms.

24. The vesicle produced by the method of claim 22.

25. A method of forming unilamellar lipid vesicles, comprising the steps of:
(a) forming a solution of short-chain phospholipids having fatty acids with fewer than 9 carbon atoms in an organic solvent;

(b) evaporating the organic solvent under nitrogen to form a film of short-chain phospholipids;

(c) dispersing the film of short-chain phospholipids in an aqueous medium;

(d) forming a solution of long-chain phospholipids having fatty acids with at least 12 carbon atoms in an organic solvent;

(e) evaporating the organic solvent under nitrogen to form a film of long-chain phospholipids;

(f) dispersing the film of long-chain phospholipids in an aqueous medium;

(g) combining the dispersion of short-chain phospholipids and the dispersion of long-chain phospholipids; and (h) equilibrating the resulting dispersion until unilamellar lipid vesicles have formed.

26. The method of claim 25 in which the short-chain phospholipids are comprised of fatty acids having 6 to 8 carbon atoms.

27. The vesicle produced by the method of claim 25.

28. A method of forming unilamellar lipid vesicles, comprising the steps of:

(a) forming a solution of short-chain phospholipids having fatty acids with fewer than 9 carbon atoms in an organic solvent;

(b) evaporating the organic solvent under nitrogen to form a first film;

(c) dispersing the first film in an aqueous medium;

(d) forming a solution of long-chain phospholipids having fatty acids with at least 12 carbon atoms and at least one additional component selected from the group consisting of cholesterol, stearylamine, phosphatidic acid, cardiolipin and lysophosphatidylcholine in an organic solvent;

(e) evaporating the organic solvent under nitrogen to form a second film;

(f) dispersing the second film in an aqueous medium;

(g) combining the dispersion of the first film and the dispersion of the second film; and (h) equilibrating the resulting dispersion until unilamellar lipid vesicles have formed.

29. The method of claim 28 in which the short-chain phospholipids are comprised of fatty acids having 6 to 8 carbon atoms.

30. The vesicle produced by the method of claim 29.

31. A unilamellar lipid vesicle comprised of short-chain phospholipids having fatty acids with fewer than 9 carbon atoms and long-chain phospholipids having fatty acids with at least 12 carbon atoms.

32. The unilamellar lipid vesicle of claim 31 in which the short-chain phospholipids are comprised of fatty acids having 6 to 8 carbon atoms.

33. A composition for the delivery of a substance comprising a unilamellar lipid vesicle of short-chain phospholipids comprised of fatty acids having 6-8 carbon atoms and long-chain phospholipids comprised of fatty acids having at least 12 carbon atoms, said unilamellar lipid vesicle encapsulating the substance.

34. A unilamellar lipid vesicle of claim 33 in which the encapsulated substance is a drug.

35. In a method of forming unilamellar lipid vesicles, the improvement comprising combining a dispersion of short-chain phospholipids having fatty acids with fewer than 9 carbon atoms in a first aqueous medium and a dispersion of long-chain phospholipids having fatty acids with at least 12 carbon atoms in a second aqueous medium and equilibrating the resulting dispersion under conditions suitable for unilamellar lipid vesicles to form.

36. A unilamellar lipid vesicle comprised of short-chain phospholipids comprised of fatty acids having 6-8 carbon atoms, long-chain phospholipids comprised of fatty acids having at least 12 carbon atoms, and at least one additional component selected from the group consisting of: cholesterol, stearylamine, phosphatidic acid, cardiolipin and lysopholsphatidylcholine.

37. Unilamellar lipid vesicles having a single lipid bilayer which is comprised of:

(a) short-chain phospholipids selected from the group consisting of dihexanoylphosphatidylcholine, diheptanoylphosphatidylcholine and dioctanoylphosphatidylcholine; and (b) long-chain phospholipids comprised of fatty acids having at least 12 carbon atoms.

* * * * *

UNITED STATES PATENT AND TRADEMARK OFFICE
CERTIFICATE OF CORRECTION

PATENT NO. : 4,921,706

DATED : May 1, 1990

INVENTOR(S) : Mary F. Roberts and Nancy E. Gabriel

It is certified that error appears in the above-identified patent and that said Letters Patent is hereby corrected as shown below:

ON THE TITLE PAGE:  item [75]

The first inventor's middle initial is "F".

Signed and Sealed this

Twenty-second Day of October, 1991

Attest:

HARRY F. MANBECK, JR.

*Attesting Officer*   *Commissioner of Patents and Trademarks*